(12) United States Patent
Vigsnæs et al.

(10) Patent No.: US 10,835,544 B2
(45) Date of Patent: *Nov. 17, 2020

(54) SYNTHETIC COMPOSITION FOR REGULATING SATIETY

(71) Applicant: GLYCOM A/S, Hørsholm (DE)

(72) Inventors: Louise Kristine Vigsnæs, København NV (DK); Bruce McConnell, La Tour de Peilz (CH); Emma Elison, Hjärup (SE)

(73) Assignee: GLYCOM A/S, Kongens Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/183,391

(22) Filed: Jun. 15, 2016

(65) Prior Publication Data

US 2017/0095491 A1 Apr. 6, 2017

Related U.S. Application Data

(63) Continuation-in-part of application No. 15/104,794, filed as application No. PCT/DK2015/050385 on Dec. 8, 2015.

(30) Foreign Application Priority Data

Dec. 8, 2014 (DK) .................................. 2014 70768

(51) Int. Cl.
*A61K 31/702* (2006.01)

(52) U.S. Cl.
CPC .................................. *A61K 31/702* (2013.01)

(58) Field of Classification Search
CPC ............................ A61K 31/702; A61K 9/0053
USPC ......................................................... 514/61
See application file for complete search history.

(56) References Cited

U.S. PATENT DOCUMENTS

| | | | |
|---|---|---|---|
| 4,895,838 A | 1/1990 | McCluer et al. | |
| 5,906,982 A | 5/1999 | Prieto et al. | |
| 2011/0189149 A1 | 8/2011 | Burcelin et al. | |
| 2011/0256233 A1* | 10/2011 | Fournell | A23C 9/1422 424/535 |
| 2012/0171165 A1 | 7/2012 | Buck et al. | |
| 2012/0208782 A1 | 8/2012 | Frantz | |
| 2012/0294840 A1 | 11/2012 | Newburg et al. | |
| 2014/0037785 A1 | 2/2014 | Barboza et al. | |
| 2015/0010670 A1 | 1/2015 | Mills et al. | |

FOREIGN PATENT DOCUMENTS

| | | | |
|---|---|---|---|
| EP | 0691079 A2 | | 1/1996 |
| EP | 0691079 A2 | * | 10/1996 |
| EP | 1332759 | | 8/2003 |
| EP | 2143341 | | 1/2010 |
| EP | 2332552 | | 6/2011 |
| WO | 98/43495 A1 | | 10/1998 |
| WO | WO0104341 | | 1/2001 |
| WO | 2007/073192 A2 | | 6/2007 |
| WO | WO2007101862 | | 9/2007 |
| WO | WO2009000803 | | 12/2008 |
| WO | 2009/077352 A1 | | 6/2009 |
| WO | 2009/082214 A1 | | 7/2009 |
| WO | WO2010115934 | | 10/2010 |
| WO | WO2010115935 | | 10/2010 |
| WO | WO2011100979 | | 8/2011 |
| WO | WO2011100980 | | 8/2011 |
| WO | 2011/119023 A1 | | 9/2011 |
| WO | WO2011119033 | | 9/2011 |
| WO | WO2012001588 | | 1/2012 |
| WO | WO2012076323 | | 6/2012 |
| WO | WO2012092153 | | 7/2012 |
| WO | WO2012107865 | | 8/2012 |
| WO | WO2012113404 | | 8/2012 |
| WO | WO2012113405 | | 8/2012 |
| WO | WO2012127410 | | 9/2012 |
| WO | WO2012155916 | | 11/2012 |
| WO | WO2012156897 | | 11/2012 |
| WO | WO2012156898 | | 11/2012 |
| WO | WO2012158517 | | 11/2012 |
| WO | WO2013036104 | | 3/2013 |
| WO | 2013/057061 A1 | | 4/2013 |
| WO | WO2013044928 | | 4/2013 |
| WO | WO2013057061 | | 4/2013 |
| WO | WO2013091660 | | 6/2013 |
| WO | WO2013139344 | | 9/2013 |
| WO | WO2013154725 | | 10/2013 |
| WO | 2014/043330 A1 | | 3/2014 |
| WO | WO2014164882 | | 10/2014 |
| WO | 2014/187464 A1 | | 11/2014 |
| WO | WO2014187464 | | 11/2014 |
| WO | WO2015071401 | | 5/2015 |
| WO | WO2015071402 | | 5/2015 |
| WO | WO2015071403 | | 5/2015 |
| WO | 2015/164021 A1 | | 10/2015 |
| WO | 2016/091265 A1 | | 6/2016 |

(Continued)

OTHER PUBLICATIONS

Anatolltou (Journal of Pediatric and Neonatal Individualized Medicine 2012;1(1):11-18).*
Asakuma et al. (European journal of clinical nutrition, (Apr. 2008) vol. 62, No. 4, pp. 488-494).*
Kresser (https://chriskresser.com/a-healthy-gut-is-the-hidden-key-to-weight-loss; Oct. 29, 2010).*

(Continued)

*Primary Examiner* — Eric Olson
*Assistant Examiner* — Michael C Henry
(74) *Attorney, Agent, or Firm* — Kunzler Bean & Adamson

(57) ABSTRACT

The application relates to synthetic compositions containing one or more human milk oligosaccharides for regulating satiety or reducing propensity to obesity.

11 Claims, No Drawings

Specification includes a Sequence Listing.

(56) References Cited

FOREIGN PATENT DOCUMENTS

| WO | 2017/129639 A1 | 8/2017 |
|---|---|---|
| WO | 2017/129641 A1 | 8/2017 |
| WO | 2017/129648 A1 | 8/2017 |
| WO | 2017/129650 A1 | 8/2017 |

OTHER PUBLICATIONS

Barile et al. (Current Opinion in Biotechnology 2013, 24:24-219).*
Druart et al. (American Society for Nutrition. Adv. Nutr. 5: 624S-633S, 2014).*
Qin, J. et al, "A human gut microbial gene catalogue established by metagenomic sequencing", Nature, vol. 464, pp. 59-65, (2010).
Ettinger, G. et al, "The influence of the human microbiome and probiotics on cardiovascular health", Gut Microbes, 5:6:719-728, (2014).
Duranti, S. et al, "Exploration of the genomic diversity and core genome of the bifidobacterium adolescentis phylogenetic group by means of a polyphasic approach", Applied and Environmental Microbiology, 79(1):336-346, (Jan. 2013).
Burcelin, R. et al, "The gut microbiota ecology: a new opportunity for the treatment of metabolic diseases?", Frontiers in Bioscience, vol. 14, pp. 5107-5117, (Jun. 2009).
Backhed, F. et al, "The gut microbiota as an environmental factor that regulates fat storage", PNAS, 101:44:15718-15723, (Nov. 2, 2004).
Qin, J. et al, "A metagenome-wide association study of gut microbiota in type 2 diabetes", Nature, vol. 490, 55-60, (Oct. 2012).
Ley, R. et al, "Microbial ecology: human gut microbes associated with obesity", Nature, vol. 444, pp. 1022-1023, (Dec. 2006).
Tremaroli, V. et al, "Functional interactions between the gut microbiota and host metabolism", Nature, 489:7415:242-249, (Sep. 2012)).
Cani, P. et al, "Changes in gut microbiota control inflammation in obese mice through a mechanism involving GLP-2-driven improvement of gut permeability", Gut, vol. 58, pp. 1091-1103, (2009).
Kootte, R. et al, "The therapeutic potential of manipulating gut microbiota in obesity and type 2 diabetes mellitus", Diabetes, Obesity & Metabolism, vol. 14, pp. 112-120, (2012).
Turnbaugh, P. et al, "An obesity-associated gut microbiome with increased capacity for energy harvest", Nature, vol. 444, pp. 1027-1031, (Dec. 2006)).
Cani P. et al, "Changes in gut microbiota control metabolic endotoxemia-induced inflammation in high-fat diet-induced obesity and diabetes in mice", Diabetes, vol. 57, pp. 1470-1481, (Jun. 2008).
Cani, P, et al, "Involvement of endogenous glucagon-like peptide-1(7-36) amide on glycaemia-lowering effect of oligofructose in streptozotocin-treated rats", J. of Endocrinology, vol. 185, pp. 457-465, (2005).
Cani, P. et al, "Metabolic endotoxemia initiates obesity and insulin resistance", Diabetes, vol. 56, pp. 1761-1772, (Jul. 2007).
Fearnley, G. et al, "Reduction of blood fibrinolytic activity in diabetes mellitus by insulin", The Lancet, 2(7111):1067, doi:10.1016/S0140-6736(59)91534-X, (Dec. 1959).
Ogston, D. et al, "Fibrinolysis in obesity", The Lancet, 284(7371):1205-1207, (Dec. 5, 1964).
Hotamisligil, G. et al, "IRS-1-mediated inhibition of insulin receptor tyrosine kinase activity in a TNF-alpha- and obesity-induced insulin resistance", Science, 271(5249):665-670, (Feb. 2, 1996).
Uysal, K. et al, "Protection from obesity-induced insulin resistance in mice lacking TNF-alpha function", Nature, vol. 389, pp. 610-614, (Oct. 9, 1997).
Amar, J. et al, "Intestinal mucosal adherence and translocation of commensal bacteria at the early onset of type 2 diabetes: molecular mechanisms and probiotic treatment", EMBO Molecular Medicine, vol. 3, pp. 559-572, (2011).
Andersson, A. et al, "Comparative analysis of human gut microbiota by barcoded pyrosequencing", PlosOne, 3(7):e2836, (Jul. 2008).
IDF Diabetes Atlas, International Diabetes Federation, 6th edition.
Urashima, T. et al, "Milk oligosaccharides", Nova Biomedical Books, NY, (2011).
Bezirtzoglou, E. et al, "Microbiota profile in feces of breast-and-formula-fed newborns by using fluorescence in situ hybridization", Anaerobe, vol. 17, pp. 478-482, (2011).
Bottacini, F. et al, "Diversity, ecology and intestinal function of bifidobacteria", Microbial Cell Factories, vol. 13, Suppl. 1, pp. S4, (2014).
Boulange, C. et al, "Impact of the gut microbiota on inflammation, obesity, and metabolic disease", Genome Medicine, 8:42, (2016).
Bridger, T., "Childhood obesity and cardiovascular disease", Paediatr. Child Health, 14(3):177-182, (2009).
Bruggencate, S. et al, "Functional role and mechanisms of sialyl-lactose and other sialyated milk oligosaccharides", Nutrition Reviews, 72(6):377-389, (2014).
Cani, P. et al, "Gut microbiota fermentation of prebiotics increases satietogenic and incretin gut peptide production with consequences for appetite sensation and glucose response after a meal", American J. of Clinical Nutrition, vol. 30, pp. 1236-1243, (2009).
Cano, P. et al, "Bifidobacterium CECT 7765 improves metabolic and immunological alterations associated with obesity in high-fat diet-fed mice", Obesity, 21(11):2310-2321, (Nov. 2013).
Chakraborti, C., "New-found link between microbiota and obesity", World J. of Gastrointestinal Pathophysiology, 6(4):110-119, (Nov. 2015).
Chichlowski M. et al, "Bifidobacteria isolated from infants and cultured on human milk oligosaccharides affect intestinal epitherial function", J. Pediatr. Gastroenterol Nutrition, 55(3):321-327, (Sep. 2012).
Conterno, L. et al, "Obesity and the gut microbiota: does up-regulating colonic fermentation protect against obesity and metabolic disease?", Genes Nutrition, 6:241-260, (2011).
Nuckols, C., "The diagnostic and statistical manual of mental disorders, fifth edition (DSM-5)", American Psychiatric Association, 5th edition, (2013).
Dinan, T. et al, "Psychobiotics: A novel class of psychotropic", Biol. Psychiatry, 74:720-726, (2013).
Ferrari, A. et al, "Burden of depressive disorders by country, sex, age, and year: Findings from the global burden of disease study 2010", PLOS Medicine, 10(11):e1001547, (Nov. 2013).
Fukuda, S. et al, "Bifidobacteria can protect from enteropathogenic infection through production of acetate", Nature, vol. 469, pp. 543-549, (Jan. 2011).
Gabrielli, O. et al, "Preterm milk oligosaccharides during the first month of lactation", Pediatrics, vol. 128, pp. e1520-e1531, (Nov. 2011).
Gill, S. et al, "Metagenomic analysis of the human distal gut microbiome", Science, 312(5778):1355-1359, (Jun. 2006).
Jokela, M. et al, "Association of metabolically healthy obesity with depressive symptoms: pooled analysis of eight studies", Molecular Psychiatry, vol. 19, pp. 1-5, (2013).
Kendler, K. et al, "Illicit psychoactive substance use, abuse and dependence in a population-based sample of Norwegian twins", Psychol. Med., 36(7):955-962, (Jul. 2006).
Matthan, N. et al, "Sex-specific differences in predictive value of cholesterol homeostasis markers and 10-year cardiovascular disease event rate in Framingham offspring study participants", J. American Heart Assn., vol. 2, pp. e005066-e005079, (2013).
Rolland-Cachera, M., "Childhood obesity: current definitions and recommendations for their use", Intl. J. of Pediatric Obesity, vol. 6, pp. 325-331, (2011).
Sanchez, M. et al, "Childhood obesity: A role for gut microbiota?", Intl. J. of Environ. Res. Public Health, vol. 12, pp. 162-175, (2015).
Savignac, H. et al, "Bifidobacteria exert strain-specific effects on stress-related behavior and physiology in BALB/c mice", Neurogastroenterology & Motility, vol. 26, pp. 1615-1627, (2014).
Schwiertz, A. et al, "Microbiota and SCFA in lean and overweight healthy subjects", Obesity, 18(1):190-195, (Jan. 2010).
Shah, M. et al, "Effects of GLP-1 on appetite and weight", Rev. Endocr. Metab. Disorder, 15(3):181-187, (Sep. 2014).
Tarr, A. et al, "The prebiotics 3'sialyllactose and 6'sialyllactose diminish stressor-induced anxiety-like behavior and colonic microbiota

(56) References Cited

OTHER PUBLICATIONS alterations: evidence for effects on the gut-brain axis", Brain Behav. Immun., vol. 15, pp. 181-215, (2015).

Verbeke, K. et al, "Towards microbial fermentation metabolites as markers for health benefits of prebiotics", Nutrition Research Reviews, vol. 28, pp. 42-66, (2015).

Walter, J. et al, "Detection and identification of gastrointestinal *Lactobacillus* species by using denaturing gradient gel electrophoresis and species-specific PCR primers", Appl. Environ. Microbiol., 66(1):297-303, (Jan. 2000).

Anonymous, "Obesity and overweight", WHO, Media Centre fact sheet, pp. 1-5, (Jan. 2015).

Zhang, C. et al, "Dietary modulation of gut microbiota contributes to alleviation of both genetic and simple obesity in children", EbioMedicine, vol. 2, pp. 966-982, (2015).

PCT/DK2017/050198, "Notification of Transmittal of the International Search Report and the Written Opinion of the International Searching Authority, or the Declaration", dated Aug. 23, 2017, 20 pages.

U.S. Appl. No. 15/183,404, Office Action Summary, dated Feb. 24, 2017.

U.S. Appl. No. 15/183,404, Final Office Action Summary, dated Sep. 11, 2017.

Anatolltou, "Human Milk Benefits and Breastfeeding", Journal of Pediatric and Neonatoal Individualized Medicine, 2012; 1(1), pp. 11-18.

Asanuma et al., "Variation of Major Neutral Oligosaccharides Levels in Human Colostrum", European Journal of Clinical Nutrition, Apr. 2008, vo. 62, No. 4, pp. 488-494.

U.S. Appl. No. 15/183,431. Office Action Summary, dated Oct. 13, 2017.

U.S. Appl. No. 15/183,404, Office Action Summary, dated Mar. 26, 2018.

U.S. Appl. No. 15/183,431, Office Action Summary, dated Apr. 12, 2018.

U.S. Appl. No. 15/183,456, Office Action Summary, dated Jan. 26, 2018.

L. Lykouras et al., "Anxiety Disorders and Obesity", Psychiatriki, Oct.-Dec. 2011; 22(4):307-13, (abstract) p. 1.

U.S. Appl. No. 15/104,794, Office Action Summary, dated May 31, 2018.

U.S. Appl. No. 15/183,404, Final Office Action Summary, dated Oct. 19, 2018.

U.S. Appl. No. 15/183,456, Final Office Action Summary, dated Sep. 10, 2018.

USPTO, "Office Action Summary", U.S. Appl. No. 15/104,794 dated Dec. 20, 2018, pp. 1-23.

G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.

David A. Fields et al., "A Narrative Review of the Associations Between Six Bioactive Components in Breast Milk and Infant Adiposity", Obesity, vol. 24 | No. 6 | Jun. 2016, pp. 1213-1221.

Stanley IP et al., "Breastfeeding and Maternal and Infant Health Outcomes in Developed Countries", AHRQ Publication No. 07-E007, Apr. 2007, pp. 1-415.

R. Rosmond et al., "The hypothalamic-pituitary-adrenal axis activity as a predictor or cardiovascular disease, type 2 diabetes and stroke" Journal of Internal Medicine 2000, 247; pp. 188-1979 (Year 2000).

R. Silvennoinen et al., "Acute Psychological Stress Accelerates Reverse Cholesterol Transport Via Corticosteroid-Dependent Inhibition of Intestinal Cholesterol Absorption", Circulation Stress 2012, 111(11) pp. 1459-1469 (Year 2012).

L. Deveza et al. "Therapeutic Angiogenesis for Treating Cardiovascular Diseases", Theranostics 2012 2(8), pp. 801-814 (Year 2012).

USPTO, "Summary of Office Action" U.S. Appl. No. 15/183,431, pp. 1-30, dated Feb. 7, 2019.

Olivia Ballard et al., "Human Milk Composition: Nutrients and Bioactive Factors", National Institutes of Health, Pediatr Clin North Am, Feb. 1, 2014, pp. 1-24.

Undurti N. Das, "Breastfeeding prevents type 2 diabetes mellitus: but, how and why?", known about and downloaded from https://academic.oup.com/ajcn/article-abstract/85/5/1436/4633161 on Nov. 12, 2019, pp. 1-2.

David A. Sela et al, "Nursing our microbiota: molecular linkages between bifidobacteria and milk oligosaccharides", National Institutes of Health, Trends Microbiol, Jul. 1, 2011, pp. 1-18.

U.S. Appl. No. 15/183,431, Office Action Summary, dated Oct. 31, 2019, pp. 1-26.

U.S. Appl. No. 15/104,794, Office Action Summary, dated Aug. 22, 2019, pp. 1-60.

U.S. Appl. No. 15/183,404, Office Action Summary, dated Aug. 2, pp. 1-29.

P. Cani et al., "Metabolic endotoxemia initiates obesity and insulin resistance", Diabetes, vol. 56, Jul. 2007, pp. 1761-1772.

G.V. Coppa et al., Oligosaccharides in 4 Different Milk Groups, Bifidobacteria, and Ruminococcus obeum, Hepatology and Nutrition, JPGN, vol. 53, No. 1, Jul. 2011, pp. 80-87.

E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.

U.S. Appl. No. 15/104,794, Office Action Summary, dated Mar. 6, 2020, pp. 1-52.

U.S. Appl. No. 15/183,404, Office Action Summary, dated Mar. 20, 2020, pp. 1-52.

J. Chen et al., "Bifidobacterium adolescentis supplementation ameliorates visceral fat accumulation and insulin sensitivity in an experimental model of the metabolic syndrome", British Journal of Nutrition Sep. 14, 2011, 107, 1429-1434.

M. Joossens et al., "Dysbiosis of the faecal microbiota in patients with Crohn's disease and their unaffected relatives", Downloaded from gut.bmj.com on Aug. 22, 2011, pp. 631-637.

D. Guyonne et al. "Effect of a fermented milk containing Bifidobacterium animalis DN-173 010 on the health-related quality of life and symptoms in irritable bowel syndrome in adults in primary care: a multicentre, randomized, double-blind, controlled trial", Alimentary Pharmacology & Therapeutics. 26. Apr. 2007, pp. 475-486.

P.J. Whorewll et al, "Efficcy of an Encasulated Probiotic Bifidobacterium infantis 35624 in Woman with Irritable Bowel Syndrome", American Journal of Gastroenterology, 2006, pp. 1581-1590.

S. Duranti et al., "Genomic Characterization and Transcriptional Studies of the Starch-Utilizing Strain Bifidobacterium adolescentis 22L", Applied and Environmental Microbiology, vol. 80 No. 19, Oct. 2014, pp. 6080-6090.

A.M. Zivkovic, "Human milk glycobiome and its impact on the infant gastrointestinal microbiota", PNAS | Mar. 15, 2011 | vol. 108 | suppl. 1 | pp. 4653-4658.

J.S. Frick et al., "Identification of Commensal Bacterial Strains That Modulate Yersinia enterocolitica and Dextran Sodium Sulfate-Induced Inflammatory Responses: Implications for the Development of Probiotics", Infection and Immunity, American Society for Microbiology, vol. 75, No. 7, Jul. 2007, pp. 3490-3497.

T. Pozo-Rubio et al., "Immunostimulatory effect of faecal *Bifidobacterium* species of breast-fed and formula-fed infants in a peripheral blood mononuclear cell/Caco-2 co-culture system", British Journal of Nutrition, 106, May 31, 2011, p. 1216-1223.

R. Martin et al., "Isolation of Bifidobacteria from Breast Milk and Assessment of the Bifidobacterial Population by PCR-Denaturng Gradient Gel Electrophoresis and Quantitative Real-Time PCR", Applied and Environmental Microbiology, vol. 75, No. 4, Feb. 2009, pp. 965-969.

G.V. Coppa et al., "Oligosaccharides in 4 Different Milk Groups, Bifidobacteria, and Ruminococcus obeum", JPGN, vol. 53, No. 1, Jul. 2011, pp. 80-87.

A. Wittmann et al., "Plasmacytoid Dendritic Cells Are Crucial in Bifidobacterium adolescentis-Mediated Inhibition of Yersinia enterocolitica Infection", PLOS, vol. 8, No. 8, Aug. 2013, pp. 1-10.

(56) References Cited

OTHER PUBLICATIONS

P. Wacklin et al., "Secretor Genotype (FUT2 gene) Is Strongly Associated with the Composition of Bifidobacteria in the Human Intestine", PLOS, vol. 6 No. 5, May 2011, pp. 1-10.

C. Hoarau et al., "Supernatant of Bifidobacterium breve induces dendritic cell maturation, activation, and survival through a Toll-like receptor 2 pathway", J Allergy Clin Immunol, vol. 117, No. 3, Mar. 2006, pp. 696-702.

L. Chen, "Therapeutic effects of four strains of probiotics on experimental colitis in mice", World J Gastroenterol Jan. 21, 2009; 15(3): pp. 321-327.

* cited by examiner

SYNTHETIC COMPOSITION FOR REGULATING SATIETY

CROSS REFERENCE TO RELATED APPLICATIONS

This is a continuation-in-part of U.S. patent application Ser. No. 15/104,794, filed Jun. 15, 2016, which is a national stage filing in accordance with 35 U.S.C. § 371 of PCT/DK2015/050385, filed Dec. 8, 2015, which claims the benefit of the priority of Denmark Patent Application No. PA 2014 70768, filed Dec. 8, 2014, the contents of each are incorporated herein by reference.

SEQUENCE LISTING

The instant application contains a Sequence Listing which has been submitted electronically in ASCII format and is hereby incorporated by reference in its entirety. Said ASCII copy, created on Sep. 14, 2016, is named 4564U 000085 SL.txt and is 1,333 bytes in size.

FIELD OF INVENTION

This invention relates to a method and composition for regulating satiety in humans, in particular in overweight or obese human individuals.

BACKGROUND TO THE INVENTION

The increasing trend of obese individuals has become a major health issue over the past several decades and World Health Organization (WHO) has declared obesity as a global epidemic. According to WHO, it was estimated that more than 1.9 billion adults were overweight in 2014, and among them, at least 600 million were obese. This means that obesity has more than doubled since 1980 worldwide (WHO, fact sheet from January 2015).

Overweight and obesity is commonly associated with accumulated abdominal visceral fat and can be related to psycho-sociological behavioural disorders. It is often associated with the development of several chronic complications, such as high fasting glucose levels (hyperglycaemia), elevated triglyceride levels (hypertriglyceridemia), low levels of high density lipoprotein (dyslipidaemia) and high blood pressure (hypertension). Individuals who meet at least three of these criteria are clinically diagnosed as having metabolic syndrome, which increases the risk of developing metabolic diseases such as type 2 diabetes and cardiovascular diseases (Boulangé et al., Genome Medicine 8, 42 (2016)).

Compelling evidence suggests that the dysbiotic gut microbiota serves as a pivotal contributing factor in the development of diet-related obesity in humans, and can effect metabolic regulation and alter energy homeostasis (Zhang et al., EBioMedicine 2, 966 (2015)). Gut microbiota is a specific entity within the body which has its own genome and whose gene pool is much more abundant than the one of its host. It has been estimated that the human intestine harbours $10^{13}$ to $10^{14}$ bacterial cells and the number of bacteria outnumbers the total number of cells in the body by a factor of 10 (Gill et al., Science 312, 1355 (2006)). The physiologic functions attributed to gut microbiota have extended to extra-intestinal tissues, such as the liver, brain and adipose tissue, constructing connections with obesity and related disorders including type 2 diabetes and cardiovascular disease. Thus, the gut microbiota has the potential to modulate energy regulation as well as systemic inflammation relevant for the pathophysiology of obesity. The extent to how the gut microbiota play a causal role in the development of obesity and metabolic diseases is unclear. However, marked differences in the gut microbiota have been observed between healthy, obese, and type 2 diabetic patients (Bäckhed et al., PNAS 101, 15718 (2004), Qin et al., Nature 490, 55 (2012)) with fewer Bacteroidetes and more Firmicutes in obese than lean people. However, this proportion has shown to change with weight loss leading to increase in the abundance of Bacteroidetes and decrease in the abundance of Firmicutes (Ley et al., Nature 444, 1022 (2006)). Additionally, specific changes at genus level has been observed with lower number of bifidobacteria in obese versus lean and diabetic versus non-diabetic individuals (Schwiertz et al., Obesity 18, 190 (2009)).

An altered gut microblota can affect food intake and appetite sensation, since gut bacteria and especially their SCFA metabolites can influence gut satiety hormone levels such as glucagon-like peptide 1 (GLP-1) and peptide YY (PYY) (Sanchez et al., Int. J. Environ. Res. Public Health 12, 162 (2015)). GLP-1 and PYY is of relevance to appetite and weight maintenance because they have action on the gastrointestinal tract as well as the direct regulation of appetite. Hence, regulation of these hormones in humans can reduce food intake, appetite and hunger, and promote fullness and satiety with the ultimate result of promoting weight loss (Shah, Rev. Endocr. Metab. Disord. 15, 181 (2014)).

Selective stimulation of specific beneficial intestinal bacteria to promote their growth and metabolic activity (e.g. production of SCFA) could be a helpful approach in creating an intestinal environment that is able to regulate appetite and food intake through gut satiety hormones such as GLP-1 and PYY. For example, a study has described that consuming inulin increased the gut microbiota fermentation, decreased appetite, improved postprandial glucose responses and higher concentrations of GLP-1 and PYY after two weeks of prebiotic treatment (Cani et al., Am. J. Clin. Nutr. 90, 1236 (2009)). However, in some individuals, inulin may provoke side effects such as bloating, abdominal pain and increased flatulence.

Human milk oligosaccharides (HMOs) are a heterogeneous mixture of soluble glycans found in human milk. They are the third most abundant solid component after lactose and lipids in human milk and are present in concentrations of 5-25 g/l (Gabrielli et al., Pediatrics 128, 1520 (2011)). HMOs are resistant to enzymatic hydrolysis in the small intestine and are thus largely undigested and unabsorbed (ten Bruggencate et al., Nutrition Reviews 72, 377 (2014)). The majority of HMO that reaches the colon serves as a substrate to shape the gut ecosystem by selectively stimulating the growth of specific beneficial bacteria. HMOs are believed to substantially modulate the infant gut microbiota and play a decisive role in the differences in the microbiota of formula-fed and breast-fed infants. These differences include the predominance of Bifidobacterium in the gut of breast-fed infants compared to a more diverse gut microbiota in formula-fed infants (Bezirtzoglou et al., Anoerobe 17, 478 (2011). This is viewed as beneficial for the Infant because strains of Bifidobacterium species and their metabolites are believed to have a positive effect on human health (Chichlowski et al., J. Pediatr. Gastroenterol. Nutr. 55, 321 (2012); Fukuda et al., Nature 469, 543 (2011)). Recently, it has also been demonstrated that some sialylated and fucosylated HMOs has a positive effect on the growth of certain strains of bifidobacteria that are typically found in both infant and adult microbiota (WO 2013/154725).

EP-A-1332759 discloses that oral doses of 2'-FL, 3'-SL, 6'-SL, LNnT and sialic acid promote insulin secretion in type 2 diabetes-model mice.

EP-A-2143341 discloses that a mixture of GOS, sialylated oligosaccharides and N-acylated oligosaccharides reduces triglyceride concentration in liver in model mice.

EP-A-2332552 discloses that 3'-SL and 6'-SL reduce/prevent fat accumulation in the liver and other organs in high-fat diet mice and rats.

WO 2013/057061 discloses a composition for increasing insulin sensitivity and/or reducing insulin resistance that contains long chain polyunsaturated fatty acids, probiotics and a mixture of oligosaccharides containing at least one of lacto-N-neotetraose (LNnT) and lacto-N-tetraose (LNT), at least one N-acetylated oligosaccharide different from LNnT and LNT, at least one sialylated oligosaccharide and at least one neutral oligosaccharide. This composition can also contain 2'-O-fucosyllactose (2'-FL). The composition is particularly adapted for use in infants who were born preterm and/or who experienced IUGR, and in pregnant women suffering from gestational diabetes. It is also stated that the composition can be given to children, adolescents and adults suffering from insulin resistance and/or type II diabetes. It is stated that the efficacy of the composition can be the result of the synergistic combination of immunity modulator effects triggered by the probiotics and the LC-PUFA through their stimulation with the specific oligosaccharide mixture.

WO 2013/036104 discloses a method for inter alia improving regulation of satiety in a human subject having an age of 0 to 36 months by feeding a nutritional composition comprising lipid globules.

Therefore, there remains a need for a safe, well tolerated and effective way of managing food intake by improving regulation of satiety.

SUMMARY OF THE INVENTION

The present invention provides synthetic compositions comprising one or more HMOs that can be advantageously used for regulating satiety in a human individual having a metabolic disorder, for example obesity, obesity induced pre-diabetes and obesity induced type 2 diabetes.

Accordingly, a first aspect of this invention relates to one or more human milk oligosaccharides for regulating satiety in a human having a metabolic disorder;

a second aspect of this invention relates to one or more human milk oligosaccharides for reducing propensity to obesity in a human having a metabolic disorder;

a third aspect of this invention relates to a synthetic composition for regulating satiety in a human having a metabolic disorder, the composition comprising an effective amount of one or more human milk oligosaccharides;

a fourth aspect of this invention relates to a synthetic composition for reducing propensity to obesity in a human having a metabolic disorder, the composition comprising an effective amount of one or more human milk oligosaccharides;

a fifth aspect of this invention provides a method for regulating satiety in a human having a metabolic disorder, the method comprising administering to the human an effective amount of one or more human milk oligosaccharides;

a sixth aspect of this invention provides a method for reducing propensity to obesity in a human having a metabolic disorder, the method comprising administering to the human an effective amount of one or more human milk oligosaccharides.

DETAILED DESCRIPTION OF THE INVENTION

It has now been surprisingly found that administration of human milk oligosaccharides (HMOs) to patient having a metabolic disorder, for example obesity, obesity induced pre-diabetes and obesity induced type 2 diabetes, preferentially increases the abundance of bifidobacteria in the gastro-intestinal tract and changes appetite sensation. The increased abundance of bifidobacteria leads to production of SCFAs through the fermentation of HMOs. These metabolites contribute to increasing production of GLP-1, which is associated with the feeling of satiety (Chakraborti, *World J. Gastrointest. Pathophysiol.* 6, 110 (2015)). Thus, it has been discovered that HMOs can, by enteral ingestion, increase the production of GLP-1, possibly through modulation of the intestinal microbiota in a human, in particular a non-infant human. As an outcome, a more beneficial intestinal microbial community can be shaped and maintained, and the regulation of satiety can be improved, leading to lower food intake. This can result in reduced propensity to obesity.

Terms and Definitions

The term "non-infant human" or "non-infant" means in the present context a human of 3 years of age and older. A non-infant human can be a child, a teenager, an adult or an elderly adult.

The term "obese human" or means that a human individual that has a body mass index (BMI), a measurement obtained by dividing the individual's weight by the square of the individual's height, over 30 kg/m$^2$, with the range 25-30 kg/m$^2$ defined as overweight.

Overweight and obesity for children and teens (human individuals aged 3-19 years old) is defined as the following: overweight is defined as a BMI at or above the 85th percentile and below the 95th percentile for children and teens of the same age and sex. Obesity is defined as a BMI at or above the 95th percentile for children and teens of the same age and sex (see: Rolland-Cachera, *Int. J. Pediatr. Obesity* 6, 325 (2011)).

The term "enteral administration" preferably means any conventional form for delivery of a composition to a human that causes the deposition of the composition in the gastro-intestinal tract (including the stomach). Methods of enteral administration include feeding through a naso-gastric tube or jejunum tube, oral, sublingual and rectal.

The term "oral administration" preferably means delivery into the gastrointestinal tract through the oral cavity. As such, oral administration is a form of enteral administration.

The term "effective amount" preferably means an amount of a human milk oligosaccharide sufficient to render a desired treatment outcome in a patient. An effective amount can be administered in one or more doses to the patient to achieve the desired treatment outcome. In some embodiments, the term "effective amount" may mean an amount of a single HMO, or a combination of different HMOs that is capable of increasing the abundance of bifidobacteria in the gastro-intestinal tract of a human individual of the invention, preferably, relative abundance of members of the *Bifidobacterium adolescentis* phylogenetic group in particular *B. adolescentis* and/or *B. pseudocatenulatum*.

The term "relative abundance of bifidobacteria" means the abundance of bifidobacteria relative to other genus in the microbiota of the gastro-intestinal tract.

The term "human milk oligosaccharide" or "HMO" preferably means a complex carbohydrate consisting of a small number, typically 3-10, of monosaccharide units attached to each other by an interglycosidic linkage that can be found in human breast milk and that can be in acidic or neutral form. More than about 200 different HMO structures are known to exist in human breast milk (Urashima et al.: *Milk Oligosaccharides*, Nova Biomedical Books, New York, 2011). HMOs can be core, fucosylated and sialylated oligosaccharides. Core HMOs are non-fucosylated neutral (that is non-charged) HMOs and consist of Glu, Gal and GlcNAc (thus devoid of Fuc and sialic acid). Examples of core HMOs include lacto-N-tetraose (LNT), lacto-N-neotetraose (LNnT), lacto-N-neohexaose (LNnH), lacto-N-hexaose (LNH) and p-lacto-N-neohexaose (pLNnH). Fucosyl HMOs are fucosylated lactoses or fucosylated core HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated core HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). Examples for sialylated and fucosylated HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

"Microbiota", "microflora" and "microbiome" preferably mean a community of living microorganisms that typically inhabits a bodily organ or part, particularly the gastro-intestinal organs of non-infant humans. The most dominant members of the gastrointestinal microbota include microorganisms of the phyla of *Firmicutes, Bacteroidetes, Actinobacteria, Proteobacteria, Synergistetes, Verrucomicrobia, Fusobacteria*, and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parobacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The term "bifidobacteria" means a member of the *Bifidobacterium* genus commonly found in the human gastro-intestinal tract. Examples of bifidobacteria are *Bifidobacterium longum, Bifidobacterium bifidum*, and the members of the phylogenetic *Bifidobacterium adolescentis* group. In non-infant humans, bifidobacteria preferably include members of the phylogenetic *Bifidobacterium adolescentis* group, for example *Bifidobacterium pseudocatenulatum* and/or *Bifidobacterium adolescentis*.

The term "*Bifidobacterium* of the *Bifidobacterium adolescentis* phylogenetic group*" means a bacterium selected from a group consisting of *Bifidobacterium adolescentis, Bifidobacterium angulatum, Bifidobacterium cotenulatum, Bifidobacterium pseudocatenulotum, Bifidobacterium koshiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)).

The term "synthetic composition" designates a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition of the invention typically comprises one or more compounds, advantageously HMOs, that are capable of preferentially increasing the abundance of bifidobacteria, in particular *Bifidobacterium* of the following species: *Bifidobacterium longum, Bifidobacterium bifidum*, and/or members of the phylogenetic *Bifidobacterium adolescentis* group. In some embodiments, the synthetic composition may comprise one or more compounds or components other than HMOs that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic add using genetically modified *E. coli*.

EMBODIMENTS OF THE INVENTION

An HMO for use in
- regulating satiety in a human having a metabolic disorder, and/or
- reducing propensity to obesity in a human having a metabolic disorder, may be a single HMO or a mixture of any HMOs suitable for the purpose of the invention. Preferably, the HMO is a fucosylated or a non-fucosylated neutral HMO. More preferably, the invention relates to a mixture of HMOs, the mixture comprising at least a first HMO and at least a second HMO, wherein the first HMO is a fucosylated neutral HMO and the second HMO is a non-fucosylated neutral HMO. Particularly, the mixture of HMOs may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture of HMOs contains a fucosylated HMO selected from the list consisting of 2'-FL, 3-FL and DFL, and a non-fucosylated HMO selected from the list consisting of LNT and LNnT; advantageously the mixture comprises 2'-FL and LNnT and/or LNT. In some embodiments, the mixture of HMOs essentially consists of two neutral HMOs, e.g. a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture essentially consists of a fucosylated HMO selected from the list consisting of 2'-FL, 3-FL and DFL, and a non-fucosylated HMO selected from the list consisting of LNT and LNnT; in one preferred embodiment the mixture essentially consists of 2'-FL and LNnT, in another preferred embodiment the mixture essentially consists of 2'-FL and LNT.

In a preferred embodiment, a mixture of 2'-FL and LNnT may contain the amount of 2'-FL:LNnT form about 1.5:1 to about 4:1.

The synthetic composition for use in
- regulating satiety in a human having a metabolic disorder, and/or
- reducing propensity to obesity in a human having a metabolic disorder, may comprise a single HMO or a mixture of any HMOs suitable for the purpose of the invention as disclosed above.

The synthetic composition can take any suitable form. For example, the composition can be in the form of a nutritional composition which contains other macronutrients such as proteins, lipids or other carbohydrates. The synthetic composition can also be a pharmaceutical composition.

In one embodiment, the synthetic composition can be a nutritional composition. The nutritional composition can contain sources of protein, lipids and/or digestible carbohydrates and can be in solid, powdered or liquid forms. The composition can be designed to be the sole source of nutrition or a nutritional supplement.

Suitable protein sources include intact, hydrolysed, and partially hydrolysed protein, which can be derived from any suitable source such as milk (e.g., casein, whey), animal (e.g., meat, fish), cereal (e.g., rice, corn), and vegetable (e.g., soy, potato, pea), insect (e.g., locust) and combinations of these sources. Examples of the source of protein include whey protein concentrates, whey protein isolates, whey protein hydrolysates, add caseins, sodium casemates, calcium casemates, potassium casemates, casein hydrolysates, milk protein concentrates, milk protein isolates, milk protein hydrolysates, non-fat dry milk, condensed skim milk, soy protein concentrates, soy protein isolates, soy protein hydrolysates, pea protein concentrates, pea protein isolates, pea protein hydrolysates, collagen proteins, and combinations of these sources.

The amount of protein is preferably sufficient to provide about 5% to about 30% of the energy of the nutritional composition; for example about 10% to about 25% of the energy. Within these ranges, the amount of protein can vary depending upon the nutritional needs of the intended individual.

The nutritional compositions can also include free amino adds such as tryptophan, glutamine, tyrosine, methionine, cysteine, taurine, arginine, carnitine, threonine, serine and proline and combinations of these amino acids. Threonine, serine and proline are important amino adds for the production of mucin which aids gut barrier function.

Any suitable source of other carbohydrates can be used. Examples include maltodextrin, hydrolysed or modified starch or corn starch, glucose polymers, corn syrup, corn syrup solids, rice-derived carbohydrates, sucrose, glucose, fructose, lactose, high fructose corn syrup, honey, sugar alcohols (e.g., maltitol, erythritol, sorbitol, etc.), isomaltulose, sucromalt, pullulan, potato starch, slowly-digested carbohydrates, dietary fibres such as oat fibre, soy fibre, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinogalactans, glucomannan, xanthan gum, alginate, pectin, low and high methoxy pectin, cereal beta-glucans (i.e. oat beta-glucan, barley beta-glucan), carrageenan and psyllium, Fibersol™, other resistant starches, and combinations of these carbohydrate.

Preferably the carbohydrate source includes low glycaemic index carbohydrates having a GI score of 55 or below. Examples of low glycaemic index carbohydrates include sucromalt, Fibersol™ (inulin), maltodextrins having a dextrose equivalence (DE) of less than 15, rice syrup having a dextrose equivalence of less than 15, fructooligosaccharides, resistant starches, starches, fruit sourced fibres, vegetable sourced fibres, whole grains, beta-glucans, soy fibres, oat fibres, locust bean gum, konjac flour, hydroxypropyl methylcellulose, gum acacia, chitosan, arabinogalactans, xanthan gum, alginate, low and high methoxy pectin, carrageenan, psyllium, isomaltulose, glycerine and sugar alcohols.

The nutritional compositions can include carbohydrates in an amount sufficient to provide about 30% to about 70% of the energy of the composition, for example about 35% to about 65% of the energy. Within these parameters, the amount of carbohydrate can vary widely.

Suitable lipid sources include coconut oil, fractionated coconut oil, soy oil, corn oil, olive oil, safflower oil, high oleic safflower oil, medium chain triglycerides, sunflower oil, high oleic sunflower oil, palm and palm kernel oils, palm olein, canola oil, marine oils, cottonseed oils and combinations of these oils. Fractionated coconut oils are a suitable source of medium chain triglycerides. The lipids can contain polyunsaturated fatty adds such as n-3 LC-PUFA. The n-3 LC-PUFA can be a C20 or a C22 n-3 fatty add. Preferably the n-3 LC-PUFA is docosahexaenoic add (DHA, C22:6, n-3). The source of LC-PUFA can be, for example, egg lipids, fungal oil, low EPA fish oil or algal oil.

The nutritional compositions can include lipids in an amount sufficient to provide about 10% to about 50% of energy of the nutritional composition, for example about 15% to about 40% of the energy.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic add, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 μg/ml of lutein. Lycopene can be included in an amount from about 0.001 μg/ml to about 10 μg/ml, preferably about 0.0185 μg/ml to about 5 μg/ml of lycopene. Beta-carotene can comprise from about 0.001 μg/ml to about 10 μg/ml, for example about 0.034 μg/ml to about 5 μg/ml of beta-carotene. The nutritional composition can also include a source of anthocyanins. This can be in the form of a fruit or a fruit extract. Particularly useful fruits and fruit extracts include plum/prune, apple, pear, strawberry, blueberry, raspberry, cherry, and their combinations.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. 8*B. animalis* subsp. *lactis* 88-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a food, soluble powder, a liquid concentrate, or a ready-to-use formulation. The composition can be eaten, drunk or can be fed via a nasogastric. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic add are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

The nutritional composition can also be in the form of a food such as a nutritional bar, a yoghurt, etc. These forms can be produced using standard technologies and processes.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

In other embodiment, the synthetic composition may be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to humans. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antiviral agents, antibiotics, probiotics, analgesics, and anti-inflammatory agents. The proper dosage of these compositions for a human can be determined in a conventional manner, based upon factors such as severity of the lactose intolerance, immune status, body weight and age.

The synthetic composition of this invention can also be in a unit dosage form such as a capsule, tablet or sachet. For example, the composition can be in a tablet form comprising the human milk oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethylcellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet form, can also include various nutrients including macronutrients.

The unit dosage forms can be administered orally, e.g. as a tablet, capsule, or pellet containing a predetermined amount, or as a powder or granules containing a predetermined concentration or a gel, paste, solution, suspension, emulsion, syrup, bolus, electuary, or slurry in an aqueous or non-aqueous liquid, containing a predetermined concentration. Orally administered compositions can include binders, lubricants, Inert diluents, flavouring agents, and humectants. Orally administered compositions such as tablets can optionally be coated and can be formulated so as to provide sustained, delayed or controlled release of the mixture therein.

Any described above synthetic compositions comprise an effective amount one or more HMOs and any of the described above.

In one embodiment, a synthetic composition comprises an effective amount of a mixture of 2'-FL and LnNT, preferably the mass ratio between 2'-FL and LnNT in the composition is in the range from 5:1 to 1:1.

Furthermore, the invention relates to the following methods:
  a method for regulating satiety in in a human having a metabolic disorder, the method comprising administering to the human an effective amount of one or more human milk oligosaccharides; and/or
  a method for reducing propensity to obesity in a human having a metabolic disorder, the method comprising administering to the human an effective amount of one or more human milk oligosaccharides.

The HMOs suitable for the purpose of the method are disclosed above.

For increasing the levels of the gut hormones GLP-1 and GLP-2 in a person, the amount of human milk oligosaccharide(s) required to be administered to the person will vary depending upon factors such as the risk and condition severity, the age of the person, the form of the composition, and other medications being administered to the person. However, the required amount can be readily set by a medical practitioner and would generally be in the range from about 10 mg to about 20 g per day, in certain embodiments from about 10 mg to about 15 g per day, from about 100 mg to about 10 g per day, in certain embodiments from about 500 mg to about 10 g per day, in certain embodiments from about 1 g to about 7.5 g per day. An appropriate dose can be determined based on several factors, including, for example, the body weight and/or condition of the patient being treated, the severity of the condition, being treated, other ailments and/or diseases of the person, the incidence and/or severity of side effects and the manner of administration. Appropriate dose ranges can be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 2.5 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g per day).

Preferably, one or more HMOs or a composition comprising or essentially consisting thereof is administered to a human in need enteral, e.g. orally.

A synthetic composition of this invention can be co-administered to a patient who is also receiving a standard-of-care medication for obesity or diabetes.

EXAMPLES

Examples are now described to further illustrate the invention:

Example 1—Treating High Fat Diet Induced Obesity and Diabetes 10-week-old C57BL/6J mice (100 mice) are housed in groups of five mice per cage, with free to water. The mice are divided into 10 groups of 10 mice, one control group and 9 treatment groups. All of the mice are fed a high-fat (HF) diet (60% fat and 20% carbohydrates [kcal/100 g], or an HF diet supplemented with HMO (20 g/kg of diet) for 8 weeks. Food and water intake are recorded twice a week. The 9 treatment groups are each administered one of the following: a) 2'-FL, b) 3-FL, c) 3'-SL, d) 6'-SL, e) LNT, f) LNnT, g) LNFP-I, h) DSLNT and i) a combination of these saccharides. The control group is administered the HF diet only.

Intraperitoneal or oral glucose tolerance tests are performed as follows: 6-h-fasted mice are injected with glucose into the peritoneal cavity (1 g/kg glucose, 20% glucose solution) or by gavage (3 g/kg glucose, 66% glucose solution). Blood glucose is determined with a glucose meter (Roche Diagnostics) on 3.5 µl blood collected from the tip of the tail vein. A total of 20 µl blood is sampled 30 min before and 15 or 30 min after the glucose load to assess plasma insulin concentration.

To assess intestinal permeability in vivo, the intestinal permeability of 4000 Da fluorescent dextran-FITC (DX-4000-FITC) is measured. Mice are fasted for 6 h before given DX-44-FITC by gavage (500 mg/kg body weight, 125 mg/ml). After 1 h and 4 h, 120 ml of blood is collected from the tip of the tail vein. The blood is centrifuged at 4° C., 12 000 g for 3 min. Plasma is diluted in an equal volume of PBS (pH 7.4) and analysed for DX-4000-FITC concentration with a fluorescence spectrophotometer at an excitation wavelength of 485 nm and emission wavelength of 535 nm. Standard curves are obtained by diluting FITC-dextran in non-treated plasma diluted with PBS (1:3 v/v).

Mice are anaesthetised (ketamine/xylazine, intraperineally, 100 and 10 mg/kg, respectively) after a 5 h period of fasting, and blood samples and tissues are harvested for further analysis. Mice are killed by cervical dislocation. Liver, caecum (full and empty), muscles (vastus lateralis), and adipose tissues (mesenteric and corresponding lymph nodes, epididymal, subcutaneous and visceral) are precisely dissected and weighed and stored at −80° C., for further analysis.

Total and active GLP-1 are measured from blood with ELISA (Millipore, Molsheim, France).

To assess the microbiota profile, the caecal contents collected post mortem from mice are stored at −80° C. DNA is isolated from the caecal content samples using QIAamp DNA Stool Mini Kit. The DNA concentration of extracts is measured using NanoDrop. Aliquots of 100 ng of extracted DNA are subjected to PCR using the 16S rDNA universal heteroduplex analysis (HDA) primers HDA1-GC 50-CGC-CCGGGGCGCGCCCCGGGCGGG-GCGGGGGCACGGGGGGACTCCTACGGGAGGCA-GCAGT-30 (SEQ ID NO: 1) and HDA2 50-TTACCGCGGCTGCTGGCA-30 (SEQ ID NO: 2) (both primers are disclosed in Walter et al. *Appl. Environ. Microbiol.* 66, 297 (2000)) at 56° C. for strand annealing. Initial denaturation at 94° C. for 4 min is followed by thirty cycles of 30 s at 94° C., 30 s at 56° C. and 1 min at 72° C. The quality of PCR products is verified by agarose gel electrophoresis. Amplified 16S rDNA fragments are separated by denaturing gradient gel electrophoresis (DGGE) using an INGENYphorU system equipped with 6% polyacrylamide gels with a denaturant in the range of 30-55%, where 100% denaturant is equivalent to 7M-urea and 40% formamide. Electrophoresis is carried out at 130 V for 4-5 hours at 60° C. Polyacrylamide gels are stained with GelRede nucleic add stain for 45 min, destained in ultrapure water and viewed under UV light. Bands of interest are excised from gels and lysed in ultrapure water. Extracted DNA is re-amplified using the same primers and PCR conditions. To purify the bacterial DNA, PCR products are reloaded on a denaturant gradient gel followed by excision and lysis of selected bands. DNA samples recovered from lysed bands of the second DGGE are re-amplified by PCR before purification using the QIAquick PCR Purification Kit and sequenced. Species identification is done using the Ribosomal Microbiome Database Project Classifier tool. Because of the limited sensitivity of DGGE to quantify microbial diversity, the microbial composition of DNA samples is also analysed using high-throughput sequencing. The V5-V6 region of 16S rRNA from caecal content DNA samples is amplified using the primers 784F 50-AGGATTAGATAC-CCT-GGTA-30 (SEQ ID NO: 3) and 1061R 50-CRRCAC-GAGCTGACGAC-30 (SEQ ID NO: 4) 3640 (both primers are disclosed in Andersson et al., *PloS ONE* 3, e2836 (2008)). Amplicons are pyrosequenced using a Roche 454 GS-FLX system. Sequences of at least 240 nucleotides and containing no more than two undetermined bases are retained for taxonomic assignment. The QIIME software is used for chimera check and the Greengenes database is used for classification. Bacterial diversity is determined at the phylum, family and genus levels.

The results show that HMOs are able to change the intestinal microbiota by increasing the abundance of bifidobacteria. Additionally, HMO supplementation increased the level of GLP-1 and reduced body weight and adipose tissue. The level of GLP-1 negatively correlated with food intake.

Example 2—Human Trial in Overweight and Obese Children

A total of 60 male and female patients, enrolled to a childhood obesity treatment program, are recruited to participate in the study. Patients are randomized into three groups, each of 20 patients, with 2 groups receiving different investigational products and one group receiving a placebo product for 8 weeks. The investigational products contain 4.5 grams of either 2'-FL alone or a combination of 2'-FL and LNnT while the placebo product contains 4.5 grams of glucose. All products are in powder form in a unit dosage container.

The patients are eligible to participate if: they are between 5 and 10 years of age, have a BMI SOS (Standard Deviation Score) of ≥2.0 and are enrolled in the childhood obesity treatment program at the Children's Obesity Clinic. All recruited patients and their representatives are able and willing to understand and comply with the study procedures. Patients are excluded if: they have participated in a clinical study one month prior to the screening visit and throughout the study; have any gastrointestinal disease(s) that may cause symptoms or may interfere with the trial outcome; have other severe disease(s) such as malignancy, kidney disease or neurological disease; have psychiatric disease; have used highly dosed probiotic supplements (yoghurt allowed) 3 months prior to screening and throughout the study; have consumed antibiotic drugs 3 months prior to screening and throughout the study; and consume on a regular basis medication that might interfere with symptom evaluation 2 weeks prior to screening and throughout the study.

At the initial visit (screening) patients and their representatives are given both oral and written information about the study; the children are asked for informed assent and their representatives to sign an informed consent form.

Eligibility criteria are checked and for children who are enrolled to the study, medical history and concomitant medication are registered. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking.

The serum from the blood samples is transferred to cryotubes and stored at −80° C. The following biomarkers are measured; Lipopolysaccharides (LPS), hsCRP, free fatty acids, total cholesterol, HDL, LDL, HbA1c, glucose, insulin, triglycerides, TNF-α, IL-1β, IL-6, IL-8, IL-10, GLP-1, GLP-2, Adiponectin, and Zonulin.

Equipment for collecting faecal samples is distributed. The faecal samples are stored at −80° C. until analysis. Microbiological analysis is performed on the faecal samples using 16S rRNA gene sequencing.

The Gastrointestinal Symptom Rating Scale (GSRS) questionnaire is completed on site by the participating child's representative(s), and the Bristol Stool Form Scales (BSFS) is distributed to the participant's representative(s) with instructions to assess the stool consistency during the study and at each faecal sampling point using the BSFS.

At the second visit (randomization), patients and their representatives are asked about adverse events, faecal samples are collected and equipment for collection of new samples is distributed. BSFS is collected and new BSFS is distributed. Study products are distributed together with a compliance form (diary). Patients and their representatives are reminded to follow the healthy dietary habits.

The study runs for 8 weeks with the patients consuming either a placebo or one of two investigational products daily. Patients are instructed to consume the products in the morning with breakfast. Compliance is monitored via a compliance form (diary) to be filled in daily.

Four weeks after commencement there is an intermediate check. Patients and their representatives are asked about adverse events and any changes in the patient's usual medication. Faecal samples are collected and equipment for collection of new samples is distributed. Blood pressure, pulse rate, waist and hip circumference, height and bodyweight are measured and BMI SDS calculated. The GSRS is completed on site by the participating child's representative. The BSFS is collected and new BSFS is distributed to the participant's representative(s) with instructions to assess the stool consistency at each faecal sampling point using the BSFS. Patients and their representatives are reminded to follow the healthy dietary habits.

At the end of intervention (8 weeks), each patient has a visit with the medical team. Patients and their representatives are asked about adverse events and any changes in the patient's usual medication. Study products and compliance forms are collected to check compliance. BSFS and faecal samples are collected and equipment for collection of new samples is distributed. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking, and equipment for collecting faecal samples is distributed. The GSRS questionnaire is completed on site by the participating child's representative (s).

To examine potential long term effects of the intervention, an un-blinded follow-up period follows with a visit 8 weeks after end of intervention. A physical examination is done and pubertal staging is determined. Blood pressure, pulse rate, height and bodyweight are measured, and body composition is determined by a DXA (dual energy x-ray absorptiometry)-scan and bioimpedance. BMI SDS is calculated, waist and hip circumferences measured and food intake registered. Fasting blood samples are collected for safety and biomarker studies and for biobanking. Faecal samples are collected.

The results show that oral ingestion of HMOs modulate the intestinal microbiota, and specifically stimulate the growth of bifidobacteria. The blood biomarker analysis indicates that the patients given the investigational products have increased levels of GLP-1. The level of GLP-1 correlated positively with the abundance of bifidobacteria. Collectively, HMOs are able to increase bifidobacteria and change the intestinal environment, and by this, increasing the level of GLP-1 in obese children.

Example 3—Nutritional Composition

A ready to feed nutritional composition is prepared from water, maltodextrin, milk protein concentrate, Sucromalt, glycerine, cocoa powder, soy protein isolate, fructose, high oleic safflower oil, soy oil, canola oil, plant sterol esters, HMOs, soy lecithin, magnesium chloride, calcium phosphate, carrageenan, sodium ascorbate, potassium citrate, sodium phosphate, calcium citrate, choline chloride, potassium chloride, sodium citrate, magnesium oxide, taurine, L-carnitine, alpha-tocopheryl acetate, zinc sulphate, ferrous sulphate, niacinamide, calcium pantothenate, vitamin A palmitate, citric add, manganese sulphate, pyridoxine hydrochloride, vitamin D3, copper sulphate, thiamine mononitrate, riboflavin, beta carotene, folic add, biotin, potassium iodide, chromium chloride, sodium selenate, sodium molybdate, phytonadione, vitamin B12.

The composition has an energy density of 0.8 kcal/ml with an energy distribution (% of kcal) as follows: protein: 20%, carbohydrate: 48%, fat: 32%.

Example 4—Tablet Composition

A tablet is prepared from HMO, hydroxypropyl methylcellulose, sodium alginate, gum, microcrystalline cellulose, colloidal silicon dioxide, and magnesium stearate. All raw materials except the magnesium stearate are placed into a high shear granulator and premixed. Water is sprayed onto the premix while continuing to mix at 300 rpm. The granulate is transferred to a fluidised bed drier and dried at 75° C. The dried powder is sieved and sized using a mill. The resulting powder is then lubricated with magnesium stearate and pressed into tablets. The tablets each contain 325 mg of HMO. The tablets each have a weight of 750 mg.

Example 5—Capsule Composition

A capsule is prepared by filling about 1 g of HMO into a 000 gelatine capsule using a filing machine. The capsules are then dosed. The HMO are in free flowing, powder form.

The invention claimed is:

1. A method comprising:
   administering to a non-infant human having a metabolic disorder and being diagnosable with one or more of obesity, obesity-induced pre-diabetes, and type 2 diabetes, an effective amount of a product consisting of one or more synthetic neutral human milk oligosaccharides (HMOs) selected from lacto-N-tetraose (LNT), lacto-N-neotetraose (LNnT), 2'-fucosyllactose (2'-FL), lacto-N-fucopentaose I (LNFP-I), 3-fucosyllactose (3-FL), difucosyllactose (DFL), and combinations thereof, and optionally one or more excipients,
   increasing a relative abundance of *Bifidobacterium adolescentis* in the gastrointestinal tract of the non-infant human; and
   regulating satiety in the non-infant human.

2. The method according to claim 1, wherein the synthetic neutral HMOs are administered enterally.

3. The method according to claim 1, wherein the one or more synthetic neutral HMOs consist of at least one fucosylated HMO and at least one non-fucosylated HMO.

4. The method according to claim 3, wherein the at least one fucosylated HMO is selected from the group consisting of 2'-FL, 3-FL, and DFL, and the at least one non-fucosylated HMO is selected from the group consisting of LNT and LNnT.

5. The method according to claim 4 in which the one or more isolated synthetic neutral HMOs comprise one or more of the combinations of 2'-FL and LNnT, 2'-FL and LNT, 2'-FL, DFL and LNnT, and 2'-FL, LNT and LNnT.

6. The method according to claim 5, wherein the mass ratio of 2'-FL present to LNnT present in the selected combination is from 5:1 to 1:1.

7. A method comprising:
   administering to a non-infant human an effective amount of mixture consisting of one or more synthetic fucosylated neutral HMOs human milk oligosaccharides (HMOs), one or more synthetic non-fucosylated neutral HMOs, and optionally one or more excipients, wherein the one or more fucosylated neutral HMOs are selected from the group consisting of 2'-fucosyllactose (2'-FL), 3-fucosyllactose (3-FL), and difucosyllactose (DFL), and the one or more non-fucosylated neutral HMOs are selected from the group consisting of lacto-N-tetraose (LNT) and lacto-N-neotetraose (LNnT);
   increasing a relative abundance of *Bifidobacterium adolescentis* in the gastrointestinal tract of the non-infant human; and
   reducing a propensity of obesity in the non-infant human.

8. The method of claim 7, wherein
   the one or more fucosylated neutral HMOs comprise 2'-FL; and
   the one or more non-fucosylated neutral HMOs comprise LNnT, wherein the mass ratio of 2'-FL in the mixture to LNnT in the mixture is from 5:1 to 1:1.

9. A method of at least one of regulating satiety in a non-infant human
   having a metabolic disorder and reducing a propensity to obesity in the non-infant human
   having the metabolic disorder, the method comprising:
   increasing the relative abundance of *Bifidobacterium adolescentis* in the gastrointestinal tract of the non-infant human and increasing a level of at least one gut satiety hormone in the non-infant human, by administering to the non-infant human an effective amount of a synthetic composition consisting of one to five isolated human milk oligosaccharides (HMOs) selected from the fucosylated HMOs 2'-fucosyllactose (2'-FL), 3-fucosyllactose (3-FL), and difucosyllactose (DFL), and the non-fucosylated HMOs lacto-N-tetraose (LNT) and lacto-N-neotetraose (LNnT), and combinations thereof, and optionally one or more excipients.

10. The method of claim 9, wherein the fucosylated HMO is 2'-FL and the non-fucosylated HMO is LNnT, and wherein the mass ratio of 2'-FL to LNnT in the synthetic composition is from 5:1 to 1:1.

11. The method of claim 9, wherein the synthetic composition consists essentially of 2'-FL.

* * * * *

SEQUENCE LISTING

```
<160> NUMBER OF SEQ ID NOS: 4

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgcccggggc gcgccccggg cggggcgggg gcacgggggg actcctacgg gaggcagcag      60
t                                                                     61

<210> SEQ ID NO 2
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
ttaccgcggc tgctggca                                              18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggattagat accctggta                                             19

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
crrcacgagc tgacgac                                               17
```